United States Patent [19]

Ramin

[11] Patent Number: 5,667,768

[45] Date of Patent: Sep. 16, 1997

[54] CARE COMPOSITION TO BE APPLIED TO THE NAILS

[75] Inventor: Roland Ramin, Itteville, France

[73] Assignee: L'Oreal, Paris, France

[21] Appl. No.: 718,693

[22] Filed: Sep. 27, 1996

Related U.S. Application Data

[63] Continuation of Ser. No. 421,742, Apr. 13, 1995, abandoned.

[30] Foreign Application Priority Data

Apr. 15, 1994 [FR] France .................... 94-04543

[51] Int. Cl.$^6$ ............................ A61K 7/04; A61K 7/043
[52] U.S. Cl. ................................... 424/61; 424/401
[58] Field of Search ............... 424/61, 401, 450; 514/938

[56] References Cited

U.S. PATENT DOCUMENTS 5,102,654  4/1992  Castrogiovanni et al. ............ 424/61

Primary Examiner—Thurman K. Page
Assistant Examiner—Sharon Howard
Attorney, Agent, or Firm—Finnegan, Henderson, Farabow, Garrett & Dunner

[57] ABSTRACT

The present invention relates to a care composition to be applied to the nails, comprising compounds which are capable of aiding their restructuring and enhancing their appearance.

21 Claims, No Drawings

CARE COMPOSITION TO BE APPLIED TO THE NAILS

This is a continuation of application Ser. No. 08/421,742, filed Apr. 13, 1995, now abandoned.

The present invention relates to a care composition for application to the nails.

It is known to prepare nail varnishes from, for example, a mixture of polymer, plasticizer and rheological agents in an organic solution. Varnishes are thus obtained which apply easily to the nails and give relatively good coverage and adhesion, depending on the nature of the polymer/plasticizer combination used.

It is also known to incorporate into these varnishes, which may or may not contain coloured pigments, active agents such as hardeners so as to obtain nail care bases which may be applied as an undercoat for a solvent varnish, or as they are.

However, it has been observed that although the bases thus obtained may have an action on the nails, namely, for example, hardening them, they do not allow any modification and/or improvement of the structure of the nails.

Thus, if such bases are applied to fragile nails, for example, soft nails which have a tendency to split, harder nails may be obtained but they will still have a tendency to crack and break.

The object of the present invention is to provide a composition which makes it possible to improve the external appearance of the nails, for example by moisturizing, nourishing and hardening them, while at the same time restructuring them, that is to say decreasing their capacity to split and/or to crack.

One subject of the present invention is thus a care composition for application to the nails which comprises phytanetriol and takes the form of an organic solution or a dispersion in an organic medium. The care compositions of the present invention are not emulsions.

Another subject of the present invention is a method for restructuring or moisturizing the nails, which comprises the steps of: (i) formulating a nail care composition wherein phytanetriol is included for the purpose of restructuring and/or moisturizing the nails; and (ii) applying the nail care composition to the nails.

Another subject of the invention is a method for formulating a nail care composition comprising the step of formulating a nail care composition wherein phytanetriol is included for the purpose of restructuring and/or moisturizing the nails.

Still another object of the present invention is a method for protecting the nails, which comprises the steps of: (i) formulating a nail care composition wherein phytanetriol is included for the purpose of forming a film; and (ii) applying the nail care composition wherein the film has formed to the nails.

It has been observed, surprisingly, that the use of phytanetriol in a varnish or a nail base makes it possible to obtain a care composition which is capable, after application for a certain time, of restructuring the nails by reducing their capacity to split. In the present composition, phytanetriol also has an action as a film-forming agent which is capable of covering the nails, thereby providing a possible additional protection. The composition according to the invention is thus particularly noteworthy in that it contains phytanetriol as a film-forming and/or restructuring, or even moisturizing, agent for the nails. Phytanetriol may be present in an amount preferably ranging from 0.01 to 0.5% in the final composition.

The composition according to the invention is prepared according to the state of the art.

The composition according to the invention preferably comprises a film-forming polymer in an organic solution, to which is added a plasticizer and optionally other polymers, rheological agents and thickeners.

Film-forming polymers which may preferably be used are nitrocellulose, cellulose acetobutyrate and polyvinyl butyrals, as a 5–25% solution in solvents such as toluene, xylene, ethyl acetate, esters and alcohols.

Plasticizers and other polymers which may preferably be used are acetyl tributyl citrate, dibutyl phthalate, camphor and alkyd resins, polyesters, acrylics and polyurethanes, preferably in an amount ranging from 5 to 30%.

Rheological agents and/or thickeners such as bentonite, cellulose derivatives and pyrogenic silicas may preferably be added to the composition according to the invention.

The composition may also comprise any additive which may be dissolved or dispersed in the solvent medium of the composition and which is known to those skilled in the art to be capable of being incorporated in such a composition.

Thus, if it is desired to prepare a coloured composition, common pigments, lacquers, nacre and/or dyes may be added.

Furthermore, it is possible to incorporate active agents capable of reinforcing the action of phytanetriol into the composition thus obtained, for example agents capable of treating, protecting, nourishing, hardening, revitalizing and/or moisturizing the nails.

There may, for example, preferably be mentioned N-butyl-formaldehyde for hardening, D-panthenol for nourishing and moisturizing, vitamins and derivatives thereof, keratin and derivatives thereof, cystine, chitosan and derivatives thereof, ceramides, biotin, trace elements, glycerol, protein hydrolysates, phospholipids, antifungal agents and anti-bacterial agents. These active agents may be present in an amount ranging from 0.01 to 5%.

The composition according to the invention thus consists of an organic medium which may contain particles in suspension (for example the additives or active agents which are insoluble in the organic medium), that is to say that the composition may take the form of an organic solution or a dispersion in an organic medium, which is optionally thickened.

A care composition is thus obtained which is capable of allowing, after application for a certain time of the order of several weeks, restructured, strengthened, better-nourished and better-moisturized nails to be obtained which have a decreased tendency to split and to crack, while at the same time having good, renewed flexibility.

The invention is illustrated in greater detail in the examples which follow.

EXAMPLE 1

A nail varnish having the following solids content composition was prepared:

| | |
|---|---|
| toluene | 30% |
| butyl acetate | 31.6% |
| isopropanol | 8% |
| organic acid | 0.1% |
| thickener | 1% |
| nitrocellulose | 11% |
| camphor | 1.5% |
| dibutyl phthalate | 6% |
| Santolite | 6% |

-continued

| | |
|---|---|
| alkyd resin | 4% |
| phytanetriol | 0.2% |
| pigments and nacre | 0.6% |

A nail varnish was thus obtained which applied easily to the nails and which allowed a uniform and shiny film to be obtained. The nails thus treated were observed to have a lesser tendency to crack and/or to split.

EXAMPLE 2

A nail varnish having the following solids content composition was prepared:

| | |
|---|---|
| toluene | 30% |
| butyl acetate | 31.3% |
| isopropanol | 8% |
| organic acid | 0.1% |
| thickener | 1% |
| nitrocellulose | 11% |
| camphor | 1.5% |
| dibutyl phthalate | 6% |
| Santolite | 6% |
| alkyd resin | 4% |
| phytanetriol | 0.15% |
| D-panthenol | 0.35% |
| pigments and nacre | 0.6% |

A nail varnish was thus obtained which applied easily to the nails and allowed a uniform and shiny film to be obtained.

This varnish constitutes both a make-up product and a care product for the nails, and allows the nails to be nourished and moisturized while at the same time reducing the risks of splitting.

EXAMPLE 3

A nail care base having the following composition was prepared:

| | |
|---|---|
| toluene | 21.97% |
| butyl acetate | 10% |
| ethyl acetate | 10% |
| n-propyl acetate | 10% |
| isopropanol | 25% |
| nitrocellulose | 9% |
| dibutyl phthalate | 2% |
| Santolite | 3% |
| polyvinyl butyral | 5% |
| acetyl tributyl citrate | 3% |
| UV filter | 0.5% |
| phytanetriol | 0.03% |
| N-butylformaldehyde | 0.5% |

A nail care base was obtained which is capable of strengthening and restructuring the nails.

After application 2 to 3 times per week for eight weeks, it was observed that the nails appeared to be strengthened and hardened, and had a lesser tendency to split and/or to crack.

What is claimed is:

1. A care composition for application to the nails, which comprises:
   an organic solution or a dispersion in an organic medium, said care composition containing a cosmetically effective amount of phytanetriol, wherein said care composition is substantially free of water, and further wherein said care composition is not an emulsion.

2. A composition according to claim 1, wherein said phytanetriol functions as a nail restructuring and/or moisturing agent.

3. A composition according to claim 1, wherein said phytanetriol is present in an amount ranging from 0.01 to 0.5% by weight.

4. A composition according to claim 2, which further comprises an active agent capable of reinforcing the action of phytanetriol.

5. A composition according to claim 4, wherein said active agent is capable of treating, protecting, nourishing, hardening, revitalizing and/or moisturizing the nails.

6. A composition according to claim 5, wherein said active agent is selected from N-butylformaldehyde, D-panthenol, vitamins, keratin, cystine, chitosan, ceramides, biotin, trace elements, glycerol, protein hydrolysates, phospholipids, antifungal agents and anti-bacterial agents.

7. A composition according to claim 4, wherein said active agent is present in an amount ranging from 0.01 to 5% by weight.

8. A composition according to claim 1, wherein said organic solution or said dispersion in an organic medium further comprises a film-forming polymer.

9. A composition according to claim 8, wherein said organic solution or said dispersion in an organic medium further comprises a plasticizer.

10. A composition according to claim 9, wherein said organic solution or said dispersion in an organic medium further comprises at least one additional component selected from polymers, rheological agents and thickeners.

11. A composition according to claim 8, wherein said film-forming polymer is selected from nitrocellulose, cellulose acetobutyrate and polyvinyl butyrals and is present in said composition as a 5-25% solution.

12. A composition according to claim 9, wherein said plasticizer is selected from acetyl tributyl citrate, dibutyl phthalate and camphor.

13. A composition according to claim 10, wherein said polymers are selected from alkyd resins, polyesters, acrylics and polyurethanes.

14. A method of restructuring or moisturizing the nails which comprises the steps of:
   (I) formulating a nail care composition wherein phytanetriol is included for the purpose of restructuring and/or moisturizing the nails; and
   (ii) applying said nail care composition to the nails, wherein said nail care composition is substantially free of water, and further wherein said nail care composition is not an emulsion.

15. A method of formulating a nail care composition comprising the step of formulating a nail care composition wherein phytanetriol is included for the purpose of restructuring and/or moisturizing the nails, wherein said nail care composition is substantially free of water, and further wherein said nail care composition is not an emulsion.

16. A method of protecting the nails which comprises the steps of:
   (I) formulating a nail care composition wherein phytanetriol is included for the purpose of forming a film; and
   (ii) applying said nail care composition wherein said film has formed to the nails, wherein said nail care composition is substantially free of water, and further wherein said nail care composition is not an emulsion.

17. A method according to claim 14, wherein said nail care composition is an organic solution or a dispersion in an organic medium.

18. A method according to claim 17, wherein said phytanetriol is combined with an active agent which is capable of treating, protecting, nourishing, hardening, revitalizing and/or moisturizing the nails.

19. A method according to claim 18, wherein said phytanetriol is combined with an active agent selected from N-butylformaldehyde, D-panthenol, vitamins, keratin, cystine, chitosan, ceramides, biotin, trace elements, glycerol, protein hydrolysates, phospholipids, antifungal agents and anti-bacterial agents.

20. A method according to claim 18, wherein said phytanetriol is combined with D-panthenol in order to moisturize the nails.

21. A method according to claim 18, wherein said phytanetriol is combined with N-butylformaldehyde in order to harden the nails.

* * * * *